(12) United States Patent
Phan et al.

(10) Patent No.: US 9,918,766 B2
(45) Date of Patent: Mar. 20, 2018

(54) DEVICES, METHODS AND SYSTEMS FOR AFFIXING AN ACCESS DEVICE TO A VERTEBRAL BODY FOR THE INSERTION OF BONE CEMENT

(71) Applicant: Dfine, Inc., South Jordan, UT (US)

(72) Inventors: Christopher U. Phan, Dublin, CA (US); Andrew Kohm, Foster City, CA (US); Robert Poser, Scotts Valley, CA (US); Kirti P. Kamdar, Los Gatos, CA (US)

(73) Assignee: DFine, Inc., South Jordan, UT (US)

( * ) Notice: Subject to any disclaimer, the term of this patent is extended or adjusted under 35 U.S.C. 154(b) by 997 days.

(21) Appl. No.: 13/841,380

(22) Filed: Mar. 15, 2013

(65) Prior Publication Data

US 2014/0163566 A1    Jun. 12, 2014

Related U.S. Application Data

(60) Provisional application No. 61/736,522, filed on Dec. 12, 2012.

(51) Int. Cl.
*A61B 17/88*        (2006.01)

(52) U.S. Cl.
CPC ....... *A61B 17/8811* (2013.01); *A61B 17/8805* (2013.01); *A61B 17/8808* (2013.01); *A61B 17/8816* (2013.01)

(58) Field of Classification Search
CPC ............ A61B 17/8802; A61B 17/8805; A61B 17/8822; A61B 17/8811; A61B 17/8808; A61B 17/8816; A61B 2017/564
USPC .............. 606/92–94, 260, 297, 279; 604/187
See application file for complete search history.

(56) References Cited

U.S. PATENT DOCUMENTS

| | | |
|---|---|---|
| 3,140,623 A | 7/1964 | Hoose |
| 4,411,266 A | 10/1983 | Cosman |
| 4,456,017 A | 6/1984 | Miles |
| 4,476,861 A | 10/1984 | Dimakos et al. |
| 4,595,006 A | 6/1986 | Burke et al. |
| 5,282,821 A | 2/1994 | Donahue |
| 5,284,128 A | 2/1994 | Hart |
| 5,322,505 A | 6/1994 | Krause et al. |
| 5,449,351 A | 9/1995 | Zohmann |
| 5,458,597 A | 10/1995 | Edwards et al. |
| 5,599,346 A | 2/1997 | Edwards et al. |
| 5,620,447 A | 4/1997 | Smith et al. |
| 5,628,771 A | 5/1997 | Mizukawa et al. |

(Continued)

FOREIGN PATENT DOCUMENTS

| | | |
|---|---|---|
| CN | 2841051 | 11/2006 |
| JP | 2004-242936 | 9/2004 |

(Continued)

OTHER PUBLICATIONS

European Examination Report dated May 10, 2017 for EP138623962.

*Primary Examiner* — Tatiana Nobrega
*Assistant Examiner* — Marcela I Shirsat
(74) *Attorney, Agent, or Firm* — Stoel Rives LLP

(57) ABSTRACT

Devices and method discussed for device for delivering a pressurized substance to an opening in bone within a vertebral column, useful to provide access to structures in the vertebral so that a substance, such as bone cement can be delivered through a lumen or portal or for providing access to the opening in bone by a separate instrument.

12 Claims, 16 Drawing Sheets

(56) References Cited

U.S. PATENT DOCUMENTS

| | | |
|---|---|---|
| 5,662,680 A | 9/1997 | Desai |
| 5,695,513 A | 12/1997 | Johnson et al. |
| 5,697,536 A | 12/1997 | Daniel et al. |
| 5,810,804 A | 9/1998 | Gough et al. |
| 5,833,632 A | 11/1998 | Jacobsen et al. |
| 5,851,212 A | 12/1998 | Zirps et al. |
| 5,902,251 A | 5/1999 | vanHooydonk |
| 5,921,956 A | 7/1999 | Grinberg et al. |
| 5,928,239 A | 7/1999 | Mirza |
| 5,944,715 A | 8/1999 | Goble et al. |
| 6,073,051 A | 6/2000 | Sharkey et al. |
| 6,106,524 A | 8/2000 | Eggers et al. |
| 6,123,702 A | 9/2000 | Swanson et al. |
| 6,135,999 A | 10/2000 | Fanton et al. |
| 6,231,615 B1 | 5/2001 | Preissman |
| 6,280,441 B1 | 8/2001 | Ryan |
| 6,409,722 B1 | 6/2002 | Hoey et al. |
| 6,440,138 B1 | 8/2002 | Reiley et al. |
| 6,447,506 B1 | 9/2002 | Swanson et al. |
| 6,464,683 B1 | 10/2002 | Samuelson et al. |
| 6,478,793 B1 | 11/2002 | Cosman et al. |
| 6,602,248 B1 | 8/2003 | Sharps et al. |
| 6,622,731 B2 | 9/2003 | Daniel et al. |
| 6,863,672 B2 | 3/2005 | Reiley et al. |
| 6,881,214 B2 | 4/2005 | Cosman et al. |
| 7,022,133 B2 | 4/2006 | Yee et al. |
| 7,108,696 B2 | 9/2006 | Daniel et al. |
| 7,156,843 B2 | 1/2007 | Skarda |
| 7,186,234 B2 | 3/2007 | Dahla et al. |
| 7,267,683 B2 | 9/2007 | Sharkey et al. |
| 7,270,661 B2 | 9/2007 | Dahla et al. |
| 7,480,533 B2 | 1/2009 | Cosman et al. |
| 7,503,920 B2 | 3/2009 | Siegal |
| 7,560,054 B2 | 8/2009 | Michelson |
| 7,595,634 B2 | 9/2009 | Flandre et al. |
| 7,625,364 B2 | 12/2009 | Corcoran et al. |
| 7,905,884 B2 | 3/2011 | Simonton et al. |
| 8,246,627 B2 | 8/2012 | Vanleeuwen et al. |
| 2002/0026197 A1 | 2/2002 | Foley et al. |
| 2002/0133148 A1 | 9/2002 | Daniel et al. |
| 2003/0014094 A1 | 1/2003 | Hammack et al. |
| 2003/0130664 A1 | 7/2003 | Boucher et al. |
| 2003/0212394 A1 | 11/2003 | Pearson et al. |
| 2003/0212395 A1 | 11/2003 | Woloszko et al. |
| 2004/0087936 A1 | 5/2004 | Stern et al. |
| 2005/0055030 A1* | 3/2005 | Falahee ............ A61B 17/7098 606/92 |
| 2005/0090852 A1* | 4/2005 | Layne ............... A61B 17/3417 606/190 |
| 2005/0177210 A1 | 8/2005 | Leung et al. |
| 2005/0216018 A1 | 9/2005 | Sennett |
| 2006/0025763 A1 | 2/2006 | Nelson et al. |
| 2006/0085009 A1* | 4/2006 | Truckai ............ A61B 17/7094 606/94 |
| 2006/0264819 A1 | 11/2006 | Fischer et al. |
| 2007/0055281 A1 | 3/2007 | Osorio et al. |
| 2007/0156130 A1 | 7/2007 | Thistle |
| 2008/0004615 A1 | 1/2008 | Woloszko et al. |
| 2008/0033422 A1 | 2/2008 | Turner et al. |
| 2008/0058821 A1 | 3/2008 | Maurer et al. |
| 2008/0163165 A1 | 7/2008 | Buysse et al. |
| 2008/0208255 A1 | 8/2008 | Siegal |
| 2008/0228192 A1 | 9/2008 | Beyar et al. |
| 2008/0249525 A1 | 10/2008 | Lee et al. |
| 2008/0294166 A1* | 11/2008 | Goldin ............... A61B 17/1617 606/79 |
| 2009/0131948 A1 | 5/2009 | Liu et al. |
| 2009/0264892 A1 | 10/2009 | Beyer et al. |
| 2009/0299282 A1 | 12/2009 | Lau et al. |
| 2010/0082033 A1 | 4/2010 | Germain |
| 2010/0152724 A1 | 6/2010 | Marion et al. |
| 2010/0211076 A1 | 8/2010 | Germain et al. |
| 2011/0034884 A9 | 2/2011 | Pellegrino et al. |
| 2011/0295261 A1 | 4/2011 | Germain |
| 2011/0160737 A1 | 6/2011 | Steffen et al. |
| 2011/0251615 A1 | 10/2011 | Truckai et al. |
| 2011/0295262 A1 | 12/2011 | Germain et al. |
| 2011/0301590 A1 | 12/2011 | Podhajsky et al. |
| 2012/0130381 A1 | 5/2012 | Germain |
| 2012/0330180 A1 | 12/2012 | Pellegrino et al. |
| 2012/0330301 A1 | 12/2012 | Pellegrino et al. |
| 2013/0261615 A1 | 10/2013 | Kramer et al. |
| 2013/0261621 A1 | 10/2013 | Kramer et al. |

FOREIGN PATENT DOCUMENTS

| | | |
|---|---|---|
| WO | WO 1993/004634 | 3/1993 |
| WO | WO 2003/101308 | 12/2003 |
| WO | WO 2008/076330 | 6/2008 |
| WO | WO 2008/084479 | 7/2008 |
| WO | WO 2010/039894 | 4/2010 |
| WO | WO 2010/081187 | 7/2010 |
| WO | WO 2011/137357 | 11/2011 |
| WO | WO 2011/137377 | 11/2011 |

* cited by examiner

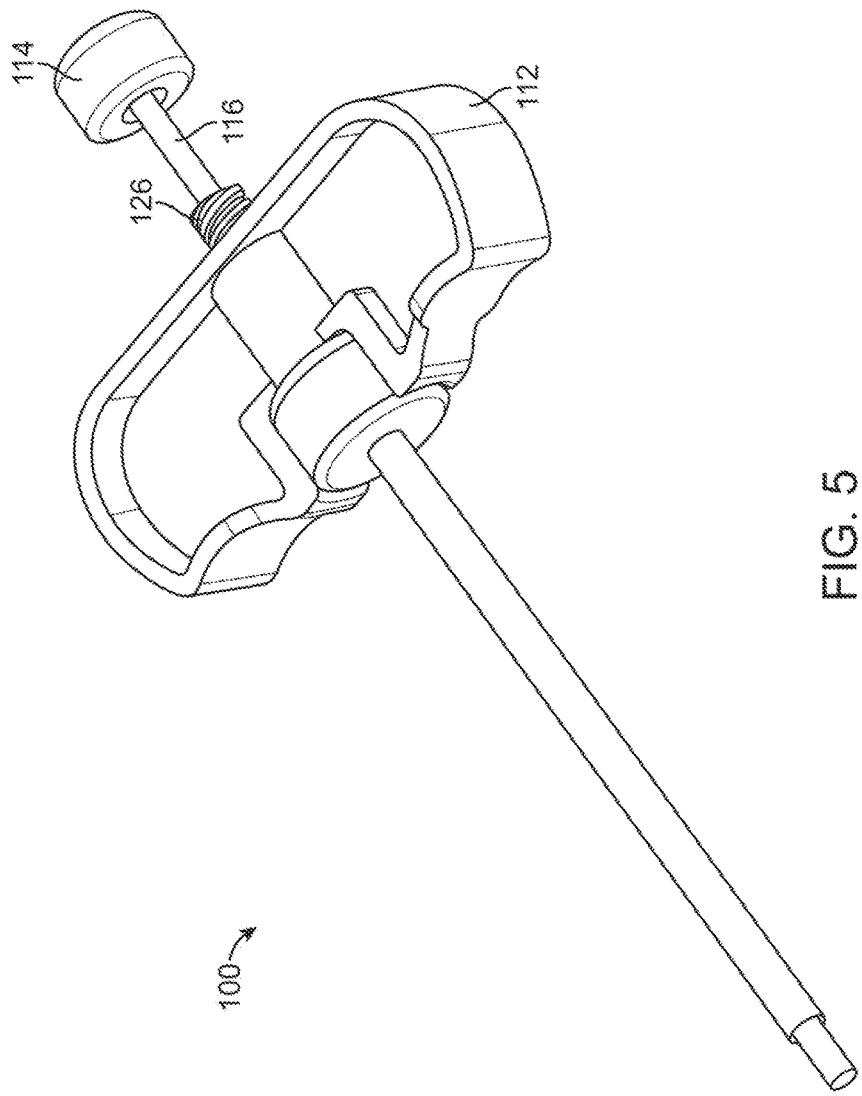

DEVICES, METHODS AND SYSTEMS FOR AFFIXING AN ACCESS DEVICE TO A VERTEBRAL BODY FOR THE INSERTION OF BONE CEMENT

RELATED APPLICATIONS

This application is a non-provisional of U.S. Provisional No. 61/736,522 filed Dec. 12, 2012, the entirety of which is incorporated by reference.

BACKGROUND OF THE INVENTION

Posterior fixation as is commonly used to help stabilize the treated spine constructs for various degenerative and traumatic spine conditions and can also be an adjunct to interbody fusion.

Posterior fixation often includes the use of a pedicle screw and rod system, where the pedicle screw is anchored into a vertebra pedicle and vertebral body. A rod is then attached between heads of at least two adjacent pedicle screws that are located ipsilaterally on the pedicle or vertebral body. This configuration helps to immobilize the treated spine construct and aid in the interbody fusion. In instances where the bone quality is poor the pedicle screw can loosen after surgery, requiring a revision surgery to replace or re-stabilize the loosened screw.

To address the anchoring problems of pedicle screws in poor quality bone, surgeons have been placing bone cement (PMMA) into the vertebral body and pedicle, then placing the pedicle screw within the bone cement. Once cured, the cement acts as a foundation for the pedicle screw allowing it to be securely anchored within the vertebral body and pedicle.

There remains a need for methods and instruments that can safely access the pedicle and deliver bone cement via a minimally invasive surgery (MIS) that can also work in conjunction with the various MIS techniques and instruments used for pedicle screw and rod fixation.

BRIEF DESCRIPTION OF THE SEVERAL VIEWS OF THE DRAWINGS

FIG. 5 illustrates a state of the device of FIG. 4 where the stylet knob is removed from the device.

SUMMARY OF THE INVENTION

Figure 1:
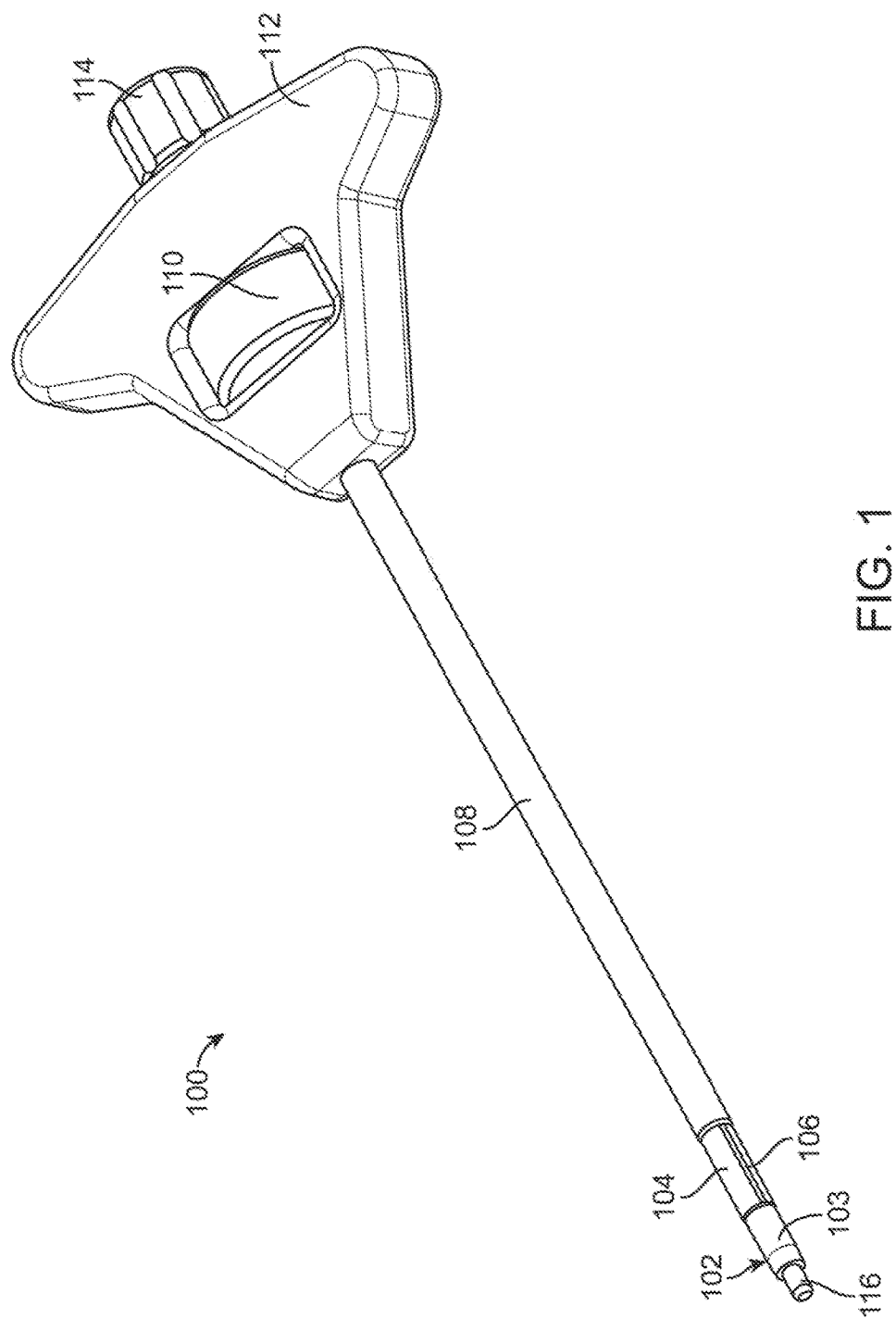
FIG. 1 shows a first variation of an access instrument for use in applying cement as described herein.

The present disclosure includes devices and methods for device for delivering a pressurized substance to an opening in bone within a vertebral column. Any of the devices and method used herein can be used for applications on or in the vertebral column (e.g., vertebral bodies, the sacrum, the coccyx, etc.) Additional variations of the device and methods allow for use anywhere in bone or other hard tissue.

In one example, a variation of a medical device described herein includes a handle portion having a proximal port; an inner member coupled to the handle portion and having a proximal end and a distal working end; a working lumen extending through the inner member; a bone engaging section located about a distal portion of the inner member, the bone engaging section configured to expand radially away from the inner member and maintain an expansion three against the opening to prevent dislodgement of the working lumen from the bone; a shuttle member mechanically coupled to the handle portion and the bone engaging section, where actuation of the shuttle member drives the bone engaging section in a radially outward direction.

In another variation, the device can further comprise an outer member and an intermediate member located between the outer member and inner member, where the bone engaging section comprises a slotted distal portion of the intermediate member.

Another variation includes a medical device further comprising a radially offset surface located on a distal portion of the inner member, where the intermediate member is coupled to the shuttle member such that actuation of the shuttle member drives the slotted distal portion of the intermediate member over the radially offset surface resulting in divergence of at the slotted distal portion in the radially outward direction.

The radially offset surface can include any surface that deflects or expands the slotted portion. For example such surfaces can be selected from the group consisting of a ramp, a protrusion, and a collar.

In an additional variation, the outer member is coupled to the shuttle and where actuation of the shuttle member causes relative movement between the outer member and intermediate member such that when slotted distal portion of intermediate member is exposed the slotted distal portion self-expands in the radially outward direction.

The slotted distal portion can comprise a plurality of tines and where the outer member causes collapse of the tines onto the inner member upon withdrawal of the slotted distal portion within the outer member. In some examples, the slotted distal portion comprises a plurality of tines where a distal end of the tines extends in the radially outward direction.

In certain devices a distal end of the inner member is coupled to a distal end of the intermediate member, where the shuttle member is coupled to the inner member and the intermediate member is coupled to the handle portion, where actuation of the shuttle member moves the distal end of the intermediate member relative to the handle portion to cause expansion of the slotted distal portion in the radially outward direction.

One example of a shuttle member comprises a threaded knob coupled to a threaded hub, where the threaded knob coupled can be coupled to one of the inner member, intermediate member, and the outer member.

The medical device described herein can further include a stylet extending in the working lumen of the inner tube, where a proximal end of the stylet is releasably coupled to the proximal port. The stylet can further include a guidewire lumen.

The disclosure also includes methods for delivering a substance to an opening located in a bone of a vertebral column. One variation of the method comprises advancing an access device to the bone, where the access device includes a delivery lumen extending from a proximal opening to a distal port; and positioning an anchoring portion of the access device within the opening in the bone; anchoring the access device to the bone by engaging the anchoring portion against a wall portion of the bone surrounding the opening such that the delivery lumen creates a fluid path from the proximal opening through the distal port and into the opening; and delivering the substance through the delivery lumen into the opening where the anchoring portion prevents rearward movement of the access device from the opening during delivery.

Variations of the method can include advancing the access device to the bone comprises advancing the access device over a guide wire, where the guide wire is positioned within the opening in bone.

In another variation, the anchoring portion comprises an expandable structure such that anchoring the access device comprises forcing the expandable structure against a wall of the hole secure the access device within the hole.

In another variation, the expandable portion comprises a slotted portion of a slidable tube, and where the access device further comprises a radially offset portion, wherein anchoring the access device comprises advancing the slidable tube over the radially offset portion to cause the slotted, portion to expand against the wall portion of the opening.

Another variation of the method includes where the delivery lumen extends through an inner tube and where the expandable portion comprises slotted portion of a slidable tube located over the inner tube, and where the inner tube is affixed to the slidable tube at a distal location, wherein anchoring the access device comprises moving the inner tube relative to the the slidable tube to cause the slotted portion to expand against the wall portion of the opening.

The disclosure also includes methods of temporarily securing an access device to an opening within a portion of bone in a vertebral column. For example, such a method can include advancing an access device to the bone, where the access device includes a delivery lumen extending from a proximal opening to a distal port; positioning a working end of the access device into the opening; and displacing an anchoring portion of the access device against a wall of the opening while maintaining the working end within the opening, wherein the anchoring portion mechanically engages the wall of the opening to releasably secure the access device to the opening.

Another method includes securing an implant within a portion of a bone in a vertebral column. Such a variation can include advancing an access device to the bone, where the access device includes a delivery lumen extending from a proximal opening to a distal port; and positioning a working end of the access device into an opening in the bone; displacing an anchoring portion of the access device against a wall of the opening while maintaining the working end within the opening, wherein the anchoring portion mechanically engages the wall of the opening to releasably secure the access device to the opening; delivering a bone cement through the delivery lumen into the opening; disengaging the anchoring portion of the access device from the wall of the opening and removing the access device from the bone; and inserting an implant into the opening.

DETAILED DESCRIPTION OF THE INVENTION

The devices and method discussed herein can accommodate the various MIS pedicle screw and rod systems placement. The devices and methods provide access to the pedicle and vertebral body so that bone cement (or any substances) can be delivered through a lumen or portal. Alternatively, the lumen can be used to insert a separate instrument for delivery of bone cement.

The devices and method described herein allow for use of a guide wire or a k-wire to locate the pedicle via a MIS approach.

The instrument's working end can expand so to accommodate pilot holes of various sizes so that the access device can be temporarily affixed within the pilot hole and securely anchored within the pedicle or vertebral body. The anchored instrument aids in the controlled and safe delivery of bone cement into the vertebral body and pedicle. The nature of the systems and devices also allow for the access device to be easily removed from the pedicle/vertebral body when the procedure is completed.

FIG. 1 shows a first variation of an access instrument 100 for use in applying cement as described herein. As shown, the access instrument 100 includes an inner tube located within a middle tube 104 and outer tube 108. The inner tube 102 can act as a working cannula to allow various instruments to be positioned therethrough. The inner tube 102 can optionally include a ramp feature 103 located at a distal end and described in detail further below. The middle tube 104 can optionally include a slotted feature 106 or other structure to allow it to advance over the ramp feature 103 to cause expansion of the middle tube 104. Clearly, the ramp feature 103 can include any feature that causes expansion of the middle tube 104. Alternate variations include a middle tube that can expand (e.g., having a shape set or similar feature) that permits expansion of the middle tube 104 as it advances without the need for a ramp feature 103 on the inner tube. The access device 100 can also include an actuation mechanism 110 that shuttles the middle tube in a distal/proximal direction. The device 100 can also include a stylet knob coupled to a removable cannulated stylet 116. The stylet 116 can optionally include features to allow the stylet to advance over a k-wire.

Figure 2A:
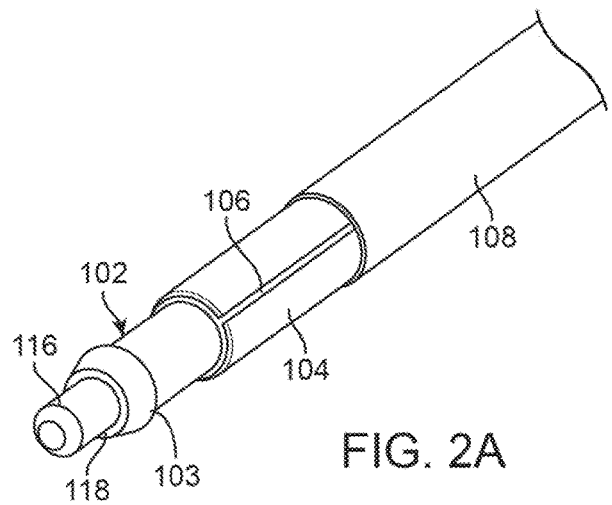
FIGS. 2A to 2C illustrate the working end of the access device shown in FIG. 1.
Figure 2B:
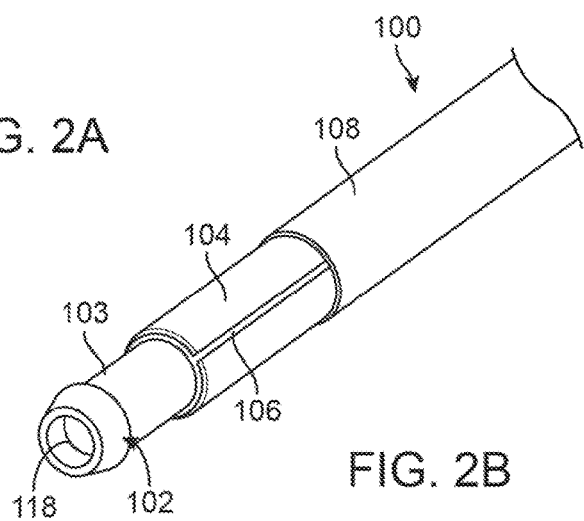
Figure 2C:
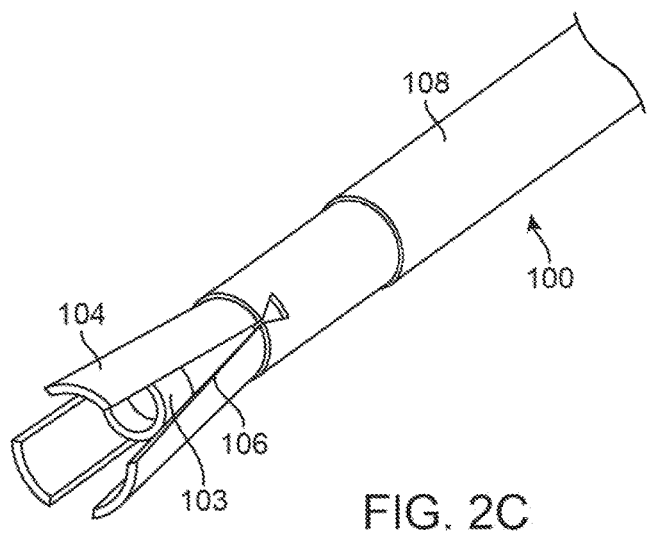

FIGS. 2A to 2C illustrate the working end of the access device 100 shown in FIG. 1. FIG. 2A illustrates the inner tube 102 having a lumen 118 that allows it to function as a working cannula. As shown, the stylet 116 is positioned through the lumen 118. FIG. 2A shows the working end or the access device 100 in an unexpanded state where the middle tube 106 is advanced out of the outer tube 108 prior to expansion over the ramp feature 103.

FIG. 2B shows the state of the access device 100 where the cannulated stylet 116 is withdrawn or otherwise removed, from the lumen 118 to allow for additional devices to be advanced therethrough or to allow for delivery of bone cement through the access device 100. FIG. 2C shows the state of the device 100 where the middle tube 105 is actuated to advance in a distal direction over the ramp feature 103 of the inner tube. Because the middle tube 104 includes one or more slots 106, the distal portion of the middle tube 104 expands as shown as it advances over the ramp feature 103. After or during the procedure, a physician can withdraw the middle tube 104 by causing proximal movement. As the middle tube 104 is moved proximally away from the ramp feature 103, the expanded portion of the middle tube 104 begins to assume its reduced profile. The proximal movement of the middle tube 104 within the outer tube 108 causes the slotted section of the middle tube to further collapse.

Figure 2D:
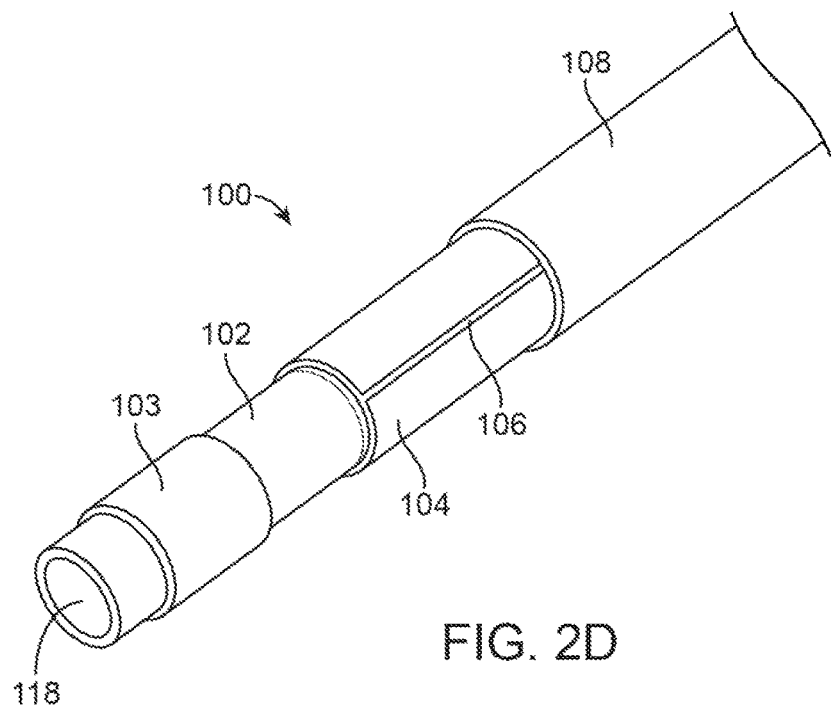
FIGS. 2D and 2E illustrate additional variations of ramp-like features.
Figure 2E:
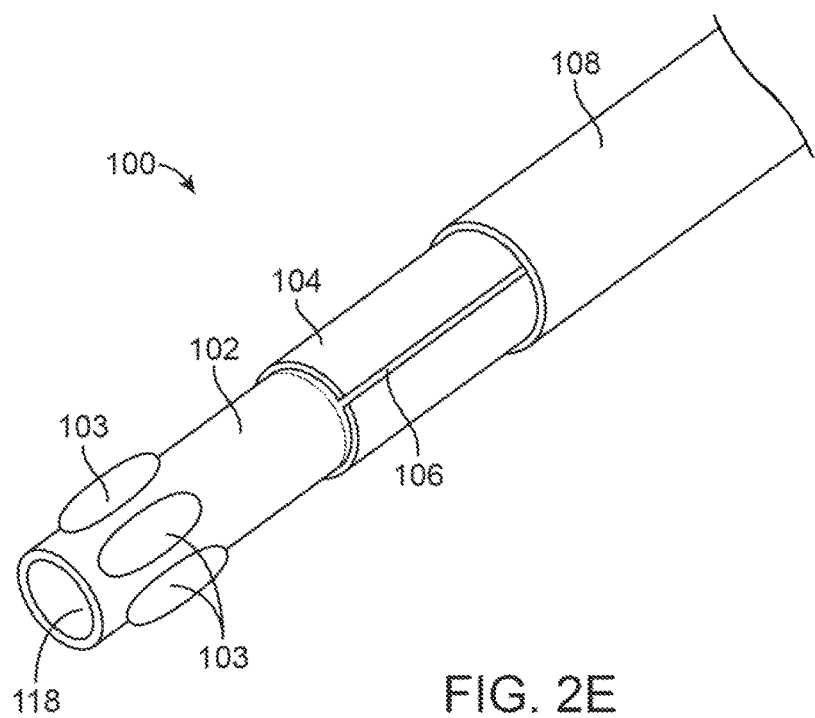

FIGS. 2D and 2E show additional variations of ramp type features on the device 100. FIG. 2D illustrates collar placed about the inner member 102. The collar 103 can have a rounded proximal end to allow the slotted portion 104 to expand or diverge when advanced relative to the collar. FIG. 2E illustrates a number of protrusions 103 forming the ramp feature. Any number of ramp features 103 can be used in the device.

Figure 3A:
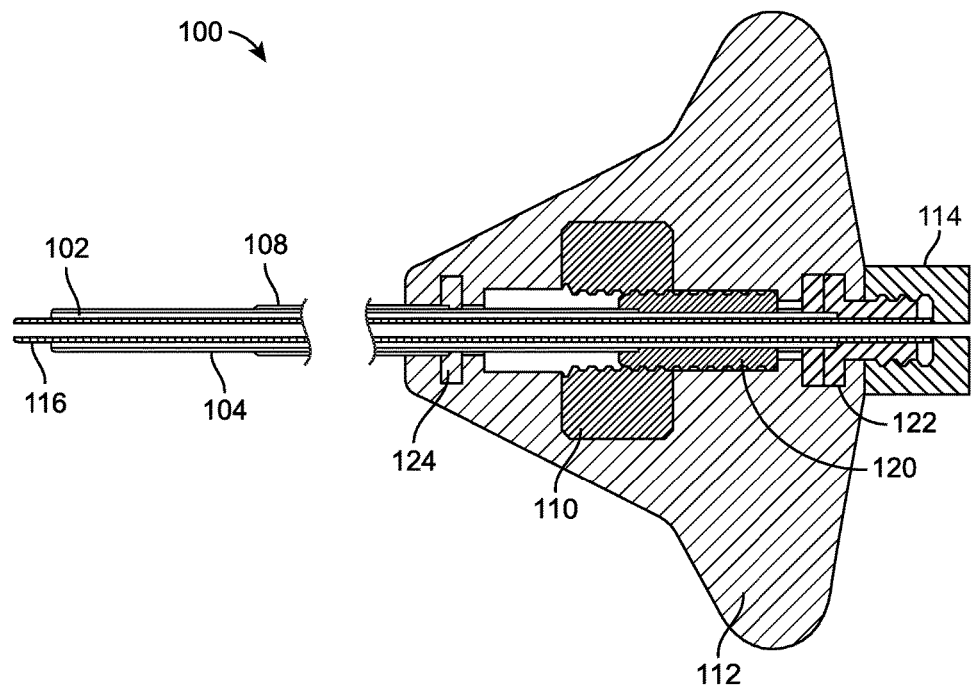
FIGS. 3A and 3B show cross sectional views of the access device shown in FIG. 1 to illustrate the mechanism that permits advancement and retraction of the middle tube.

FIG. 3A shows a cross sectional view of the access device 100 shown in FIG. 1 to illustrate the mechanism that permits advancement and retraction of the middle tube. As shown, the handle 112 includes a shuttle mechanism 110 (e.g., a knob) that is in threaded engagement with a threaded hub 120. The threaded hub 120 is attached to or otherwise affixed to the middle tube 104. Accordingly, the shuttle mechanism 110 can translate the middle tube 104 in either a distal or proximal direction through movement of the threaded hub 120. In one variation, the threaded hub can be keyed into the handle such that it prevents rotational movement of the hub relative to the handle. Such keyed feature can be mating flats between handle and hub, or pin in a slot.

Figure 3B:
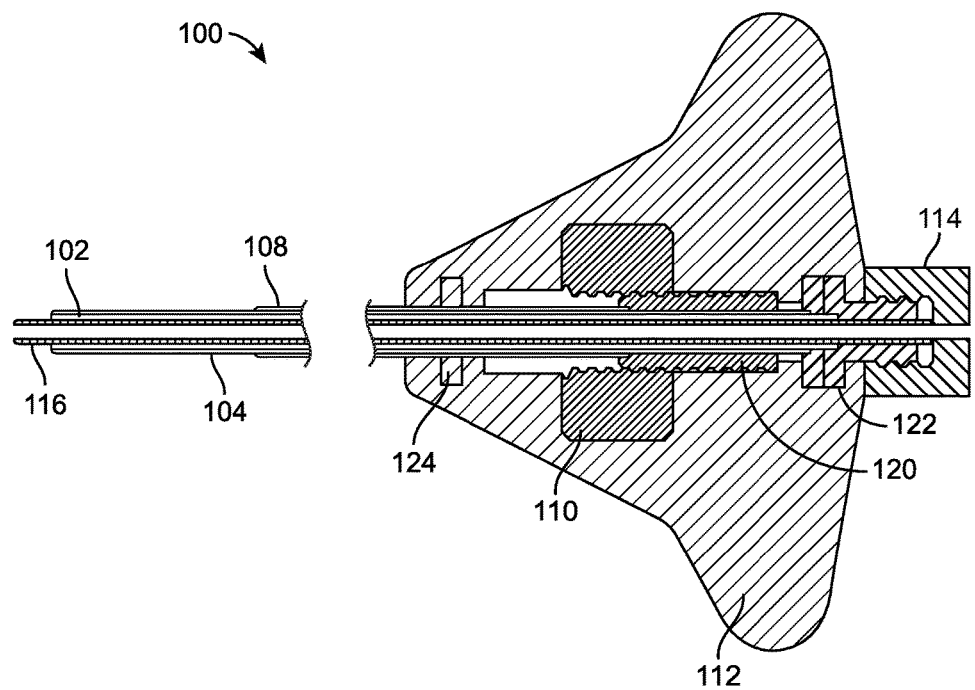

The handle 112 also includes an anchoring structure 122 that is attached to the inner tube 102 that prevents the inner tube 102 from moving as the middle tube 104 advances in a distal direction over the ramp feature. The handle 112 can also include an outer tube anchoring structure 124 at one or more points as shown in FIG. 3A. Again, the anchoring structure 124 prevents movement of the outer tube 108 as the middle tube 104 translates in a distal/proximal direction. FIG. 3A also illustrates a threaded cap or knob 114 that is affixed to the stylet 116. This threaded knob 114 can be affixed or attached to the stylet 116 so that the stylet 116 can be removed from the device 100. FIG. 3B shows a variation of the device with the shuttle mechanism 110 coupled to the outer tube 108. In such a case, the inner tube and intermediate tube can be coupled to the handle.

Figure 4:
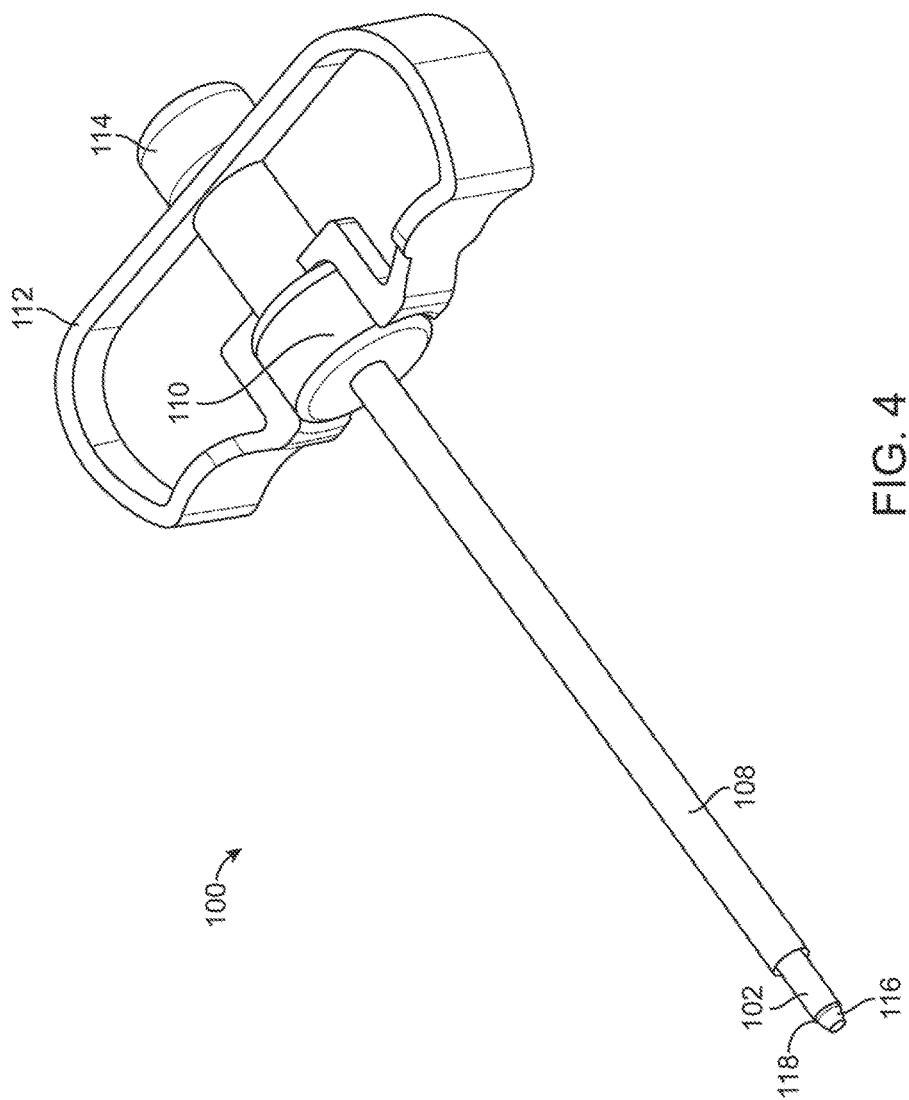
FIG. 4 shows another variation of an access device.

FIG. 4 shows another variation of an access device 100. In this variation, the access device 100 includes an inner tube 102 that functions as a working cannula that can deliver various instruments or cement through its lumen 118. The inner tube 102 is housed within a middle tube (not shown in FIG. 4) that is located within outer tube 108. In this variation, the outer tube 108 can be actuated using a shuttle mechanism 110. As with the devices described above, the access device 100 can also include a removable cannulated stylet 116 within the lumen 118 of the inner tube 102.

FIG. 5 illustrates a state of the device 100 of FIG. 4 where the stylet knob 114 can be removed from the device 100. In certain variations the stylet knob 114 is internally threaded to engage a threaded fitting 126 on the handle 112. As shown, removal of the stylet knob 114 permits removal of the stylet 116 from the device 100. Once removed, the device 100 can be coupled to any number of cement deployment systems, including those provided by DFine, Inc., San Jose, Calif.

Figure 6A:
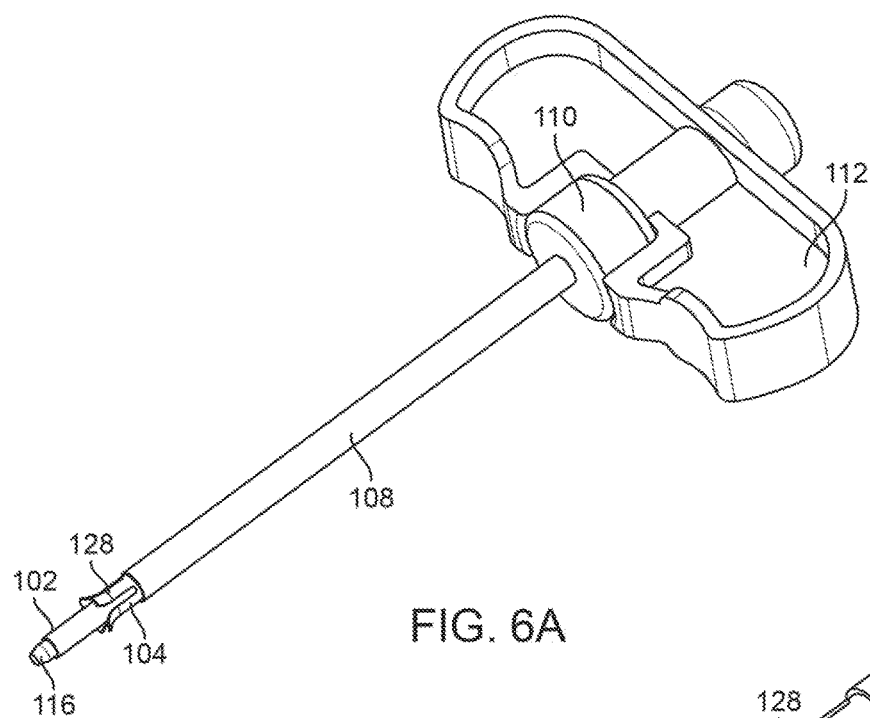
FIGS. 6A and 6B illustrate the state of the access device of FIG. 4 where the shuttle knob is used to withdraw the outer tube.
Figure 6B:
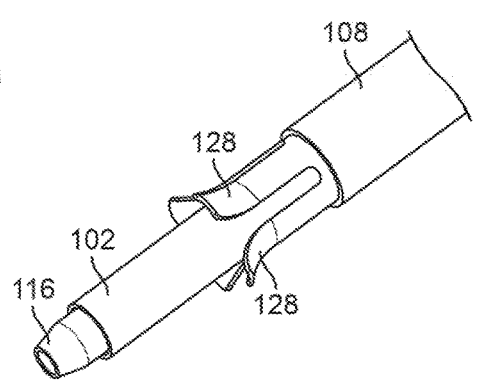

FIGS. 6A and 6B illustrate the state of the access device 100 of FIG. 4 where the shuttle knob 110 is used to withdraw the outer tube 108. As shown, the middle tube 104 includes one or more expandable section 128 that, when unconstrained by the inner tube 108, expand as shown. FIG. 6B illustrates a magnified view of the working end of FIG. 6A, where the stylet 116 is still positioned within the inner tube 102 and the outer tube 108 moves proximally to release the constraint of the expandable sections 128 of the middle tube 104. When finished with the procedure, the knob 110 can be used to extend the outer tube 108 over the expandable section 128 or tines of the middle tube 104.

Figure 7:
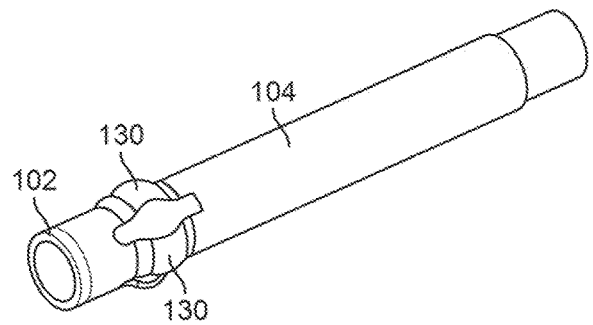
FIG. 7 shows another variation of a working end of a device.

FIG. 7 shows another variation of a working end of a device. In this example the inner tube 102 can be used to cause expansion of an expandable section 130 (in this variation expandable tines) on a middle tube 104. As shown, the inner tube 102 is affixed to an expandable middle tube 104 so that proximal and distal movement of the inner tube 102 cause respective expansion and contraction of the expandable section 130 of the middle tube 104. However, the systems and devices described herein can be used in any situation where the application of bone cement or another substance is required.

FIGS. 8A to 8K illustrate an example of a surgical technique to apply bone cement to a site where the bone cement assists in anchoring of an implant such as a pedicle screw.

Figure 8A:
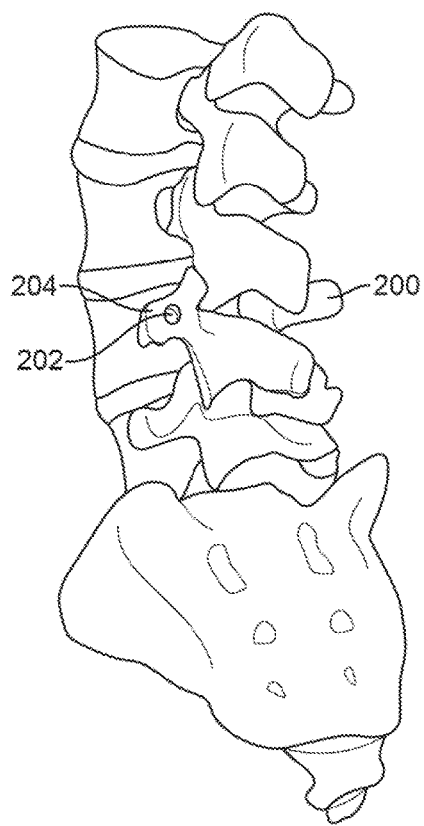
FIGS. 8A to 8K illustrate an example of a surgical technique to apply bone cement to a site where the bone cement assists in anchoring of an implant such as a pedicle screw.
Figure 8B:
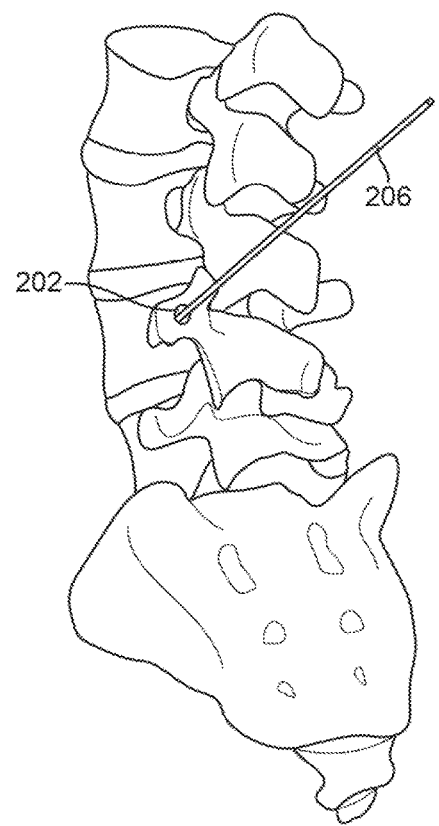
Figure 8C:
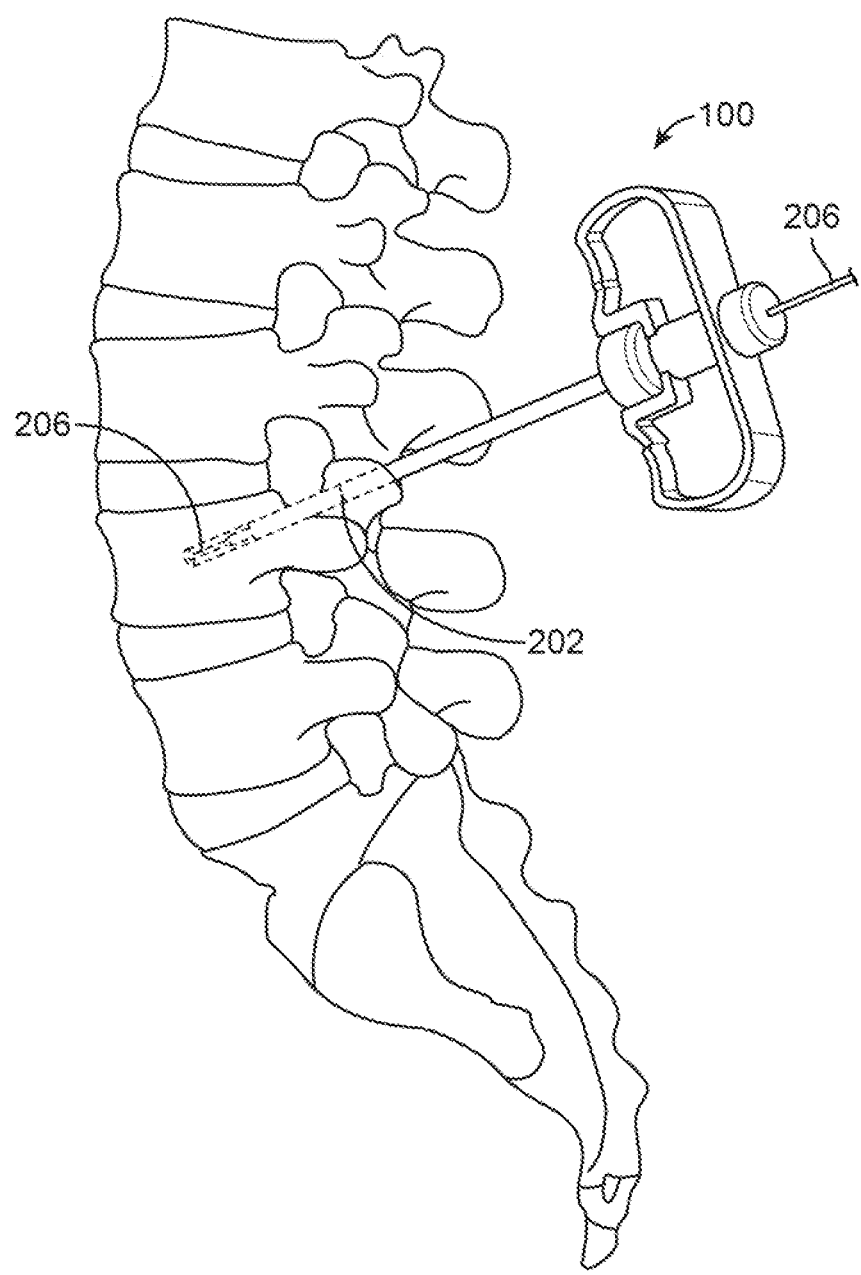

FIG. 8A illustrates a vertebral body 200 with a pilot hole 202 in a pedicle 204 created by a physician in preparation for placement of a pedicle screw system. Next. FIG. 8B shows a guide wire 206 (e.g., a 1.5 mm guide wire) placed in the pilot hole 202 using a typically preferred instrument exchange method. FIG. 8C shows an access device 100 as described herein advanced over the guide wire 206 so that the working end of the access device 100 enters the pilot hole 202. FIG. 8C illustrates the distal end of the guide wire 206 extending into the cavity of the pilot hole 202.

Figure 8D:
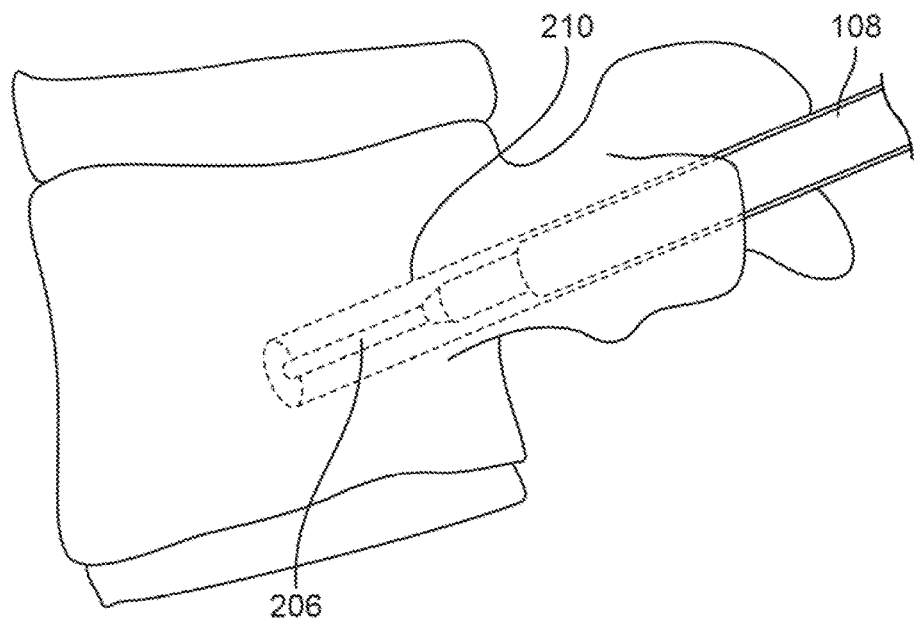
Figure 8E:
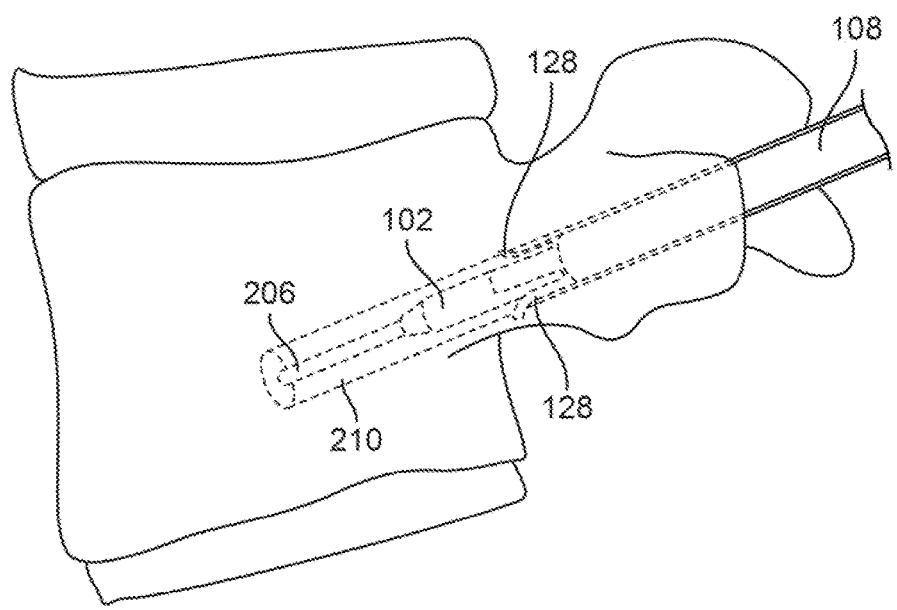

FIG. 8D shows a magnified view of the working end of the access device located within the cavity 210 of the pilot hole. When the device 100 is properly positioned in the desired anterior or posterior location, the physician can deploy the expandable section 128 so that there is a tight fit between the walls of the pilot hole cavity 210 and the expandable section 128 of the access instrument 100. As shown in FIG. 8E, this tight fit secures the access instrument 100 to the pedicle and/or vertebral body.

Figure 8F:
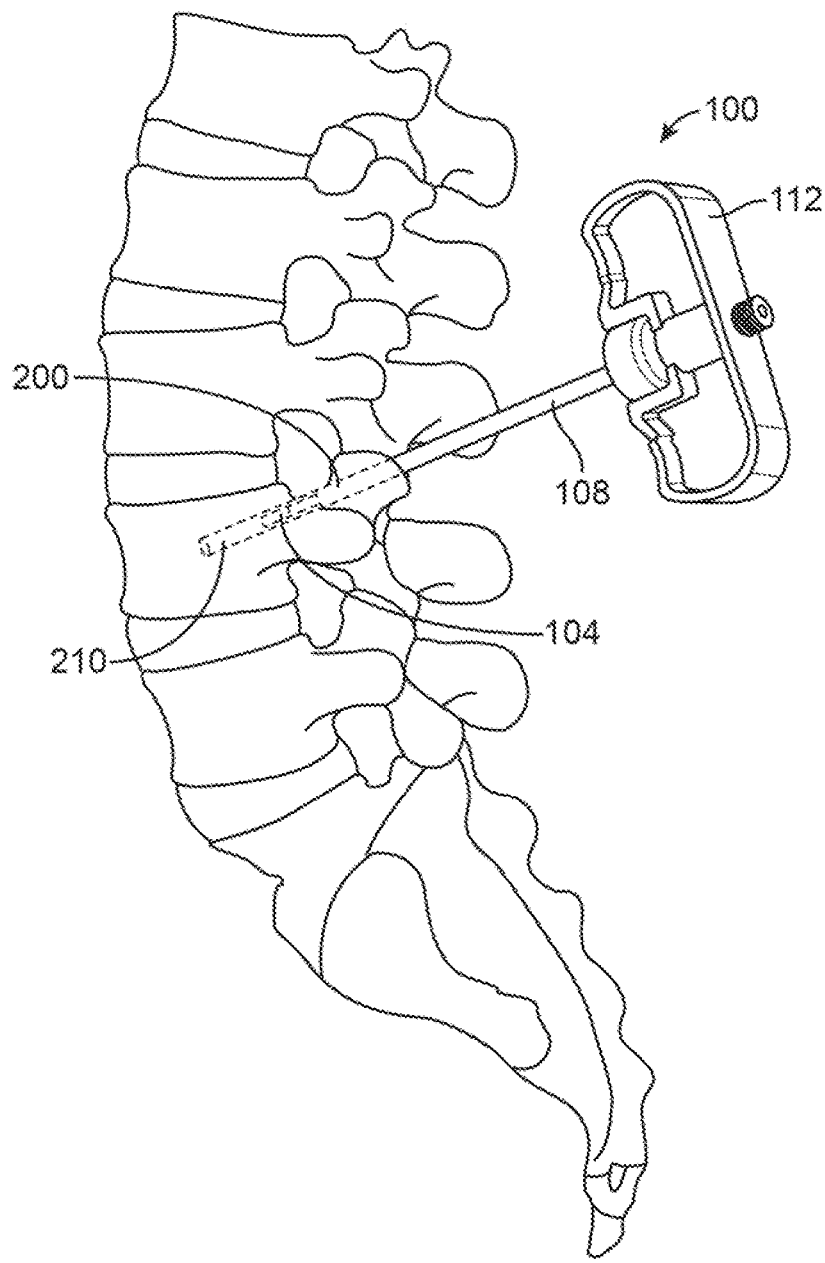
Figure 8G:
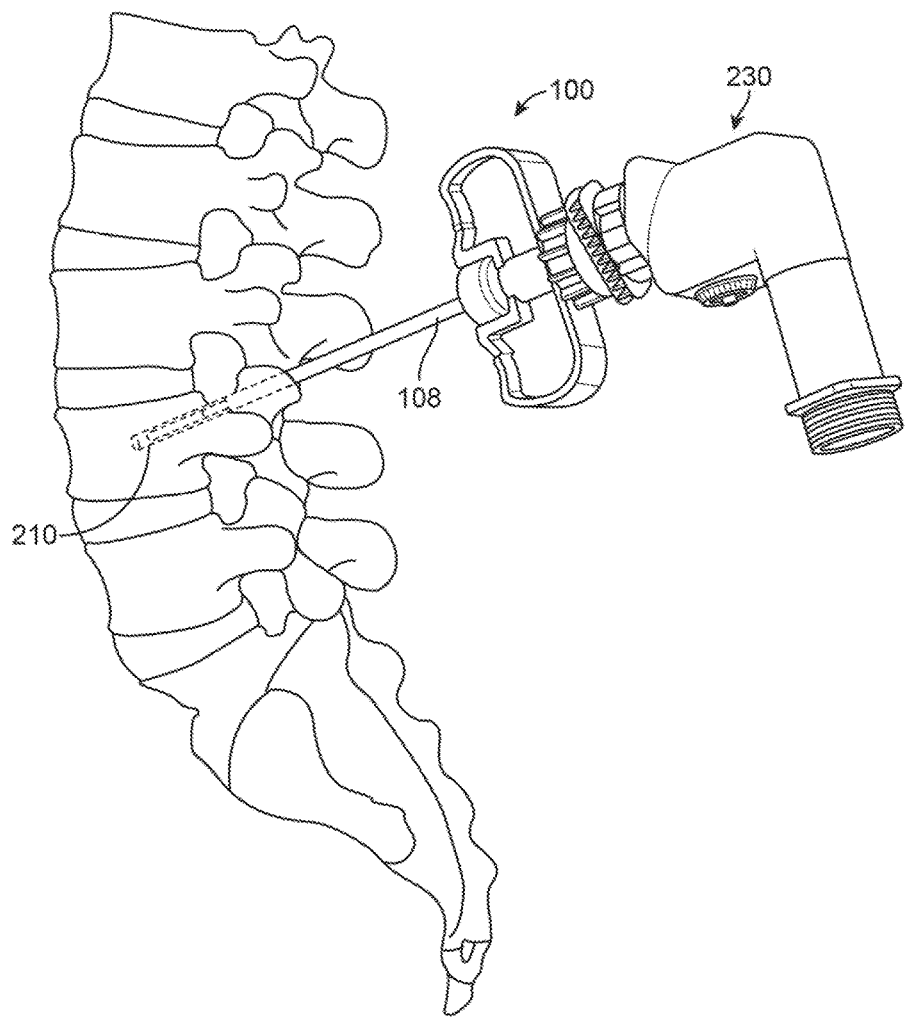
Figure 8H:
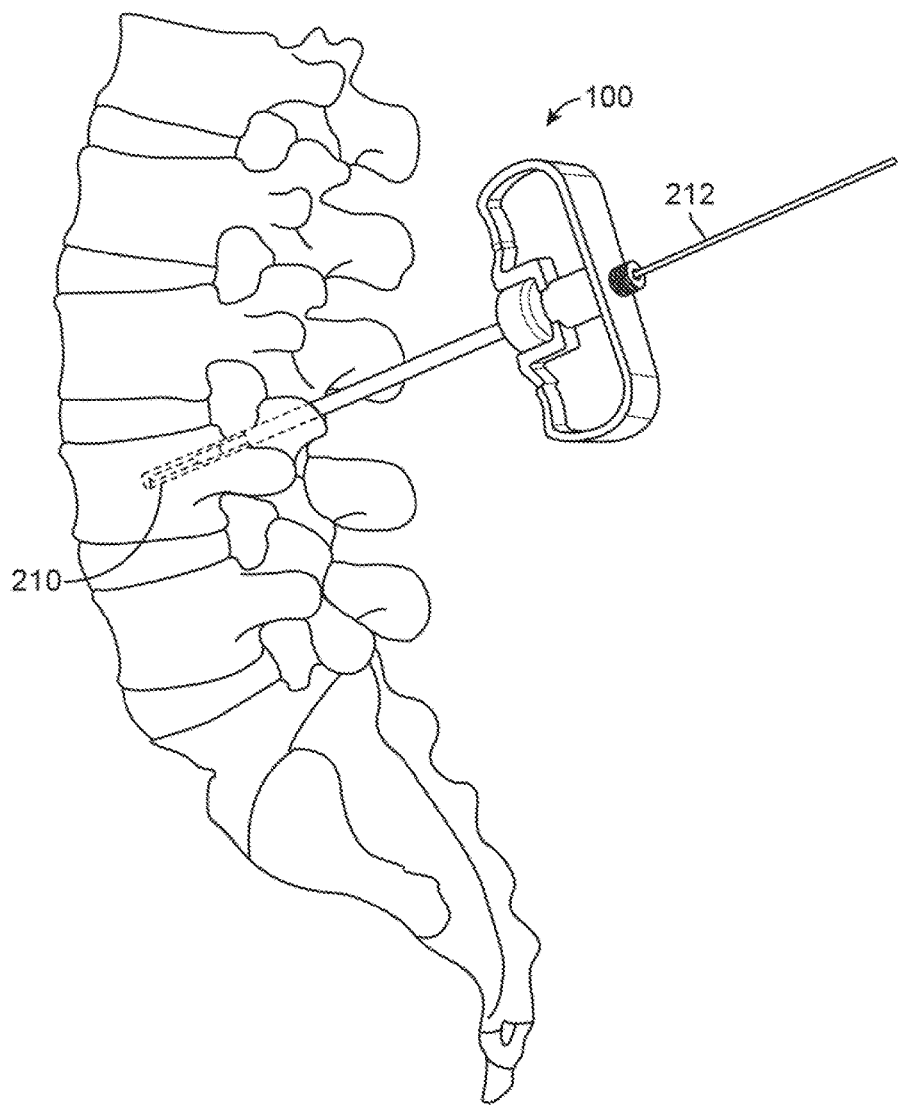

FIG. 8F shows the access device 100 secured to the vertebral body where the guidewire and stylet are removed. As mentioned above, the lumen of the inner tube creates an access path into the cavity 210 of the pilot hole 202. Next, as shown in FIG. 8G, a source of bone cement 230 can be temporarily affixed to the handle 112 of the access device 100 (e.g., by coupling to the threaded fitting 126 discussed above. The physician can then deliver the desired amount of bone cement or other substance into the cavity 210 of the pilot hole 202.

After a sufficient amount of cement is positioned into the cavity, the physician removes the source of the cement from access device 100 and inserts a guide wire 212 into the lumen of the access device 100 where the guidewire is advanced into the hone cement in the cavity 210.

Figure 8I:
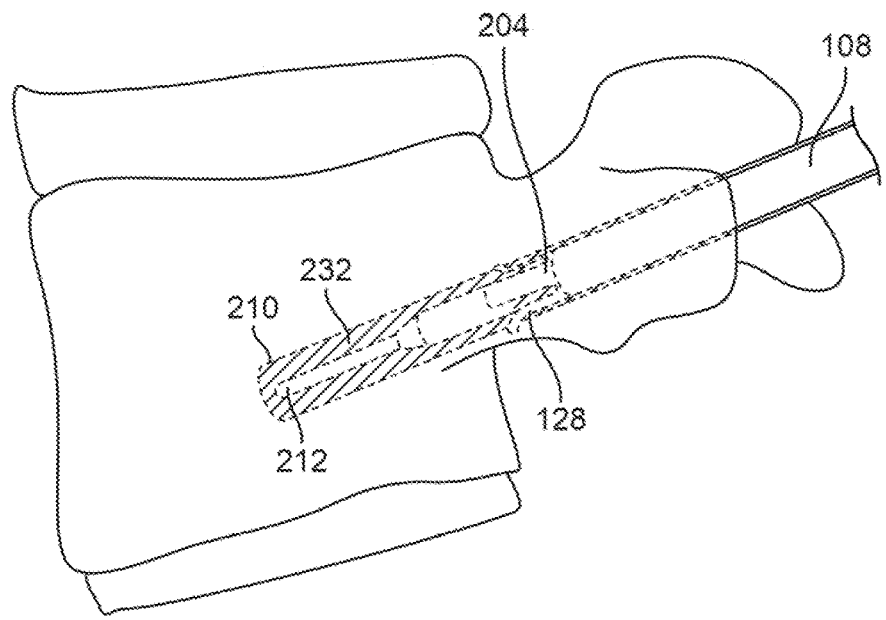
Figure 8J:
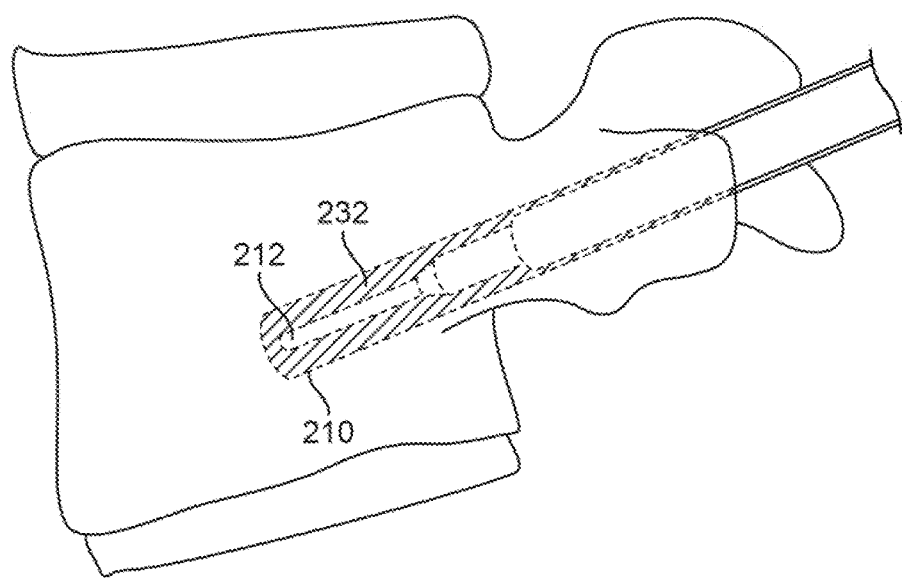

FIGS. 8I and 8J show a magnified view of the cavity 210 having bone cement 232 located therein. As shown in FIG. 8I the expandable section 128 of the middle tube 204 is still secured to the walls of the cavity 210. FIG. 8J shows the state of the device 100 after the expandable section is retracted as discussed above.

Figure 8K:
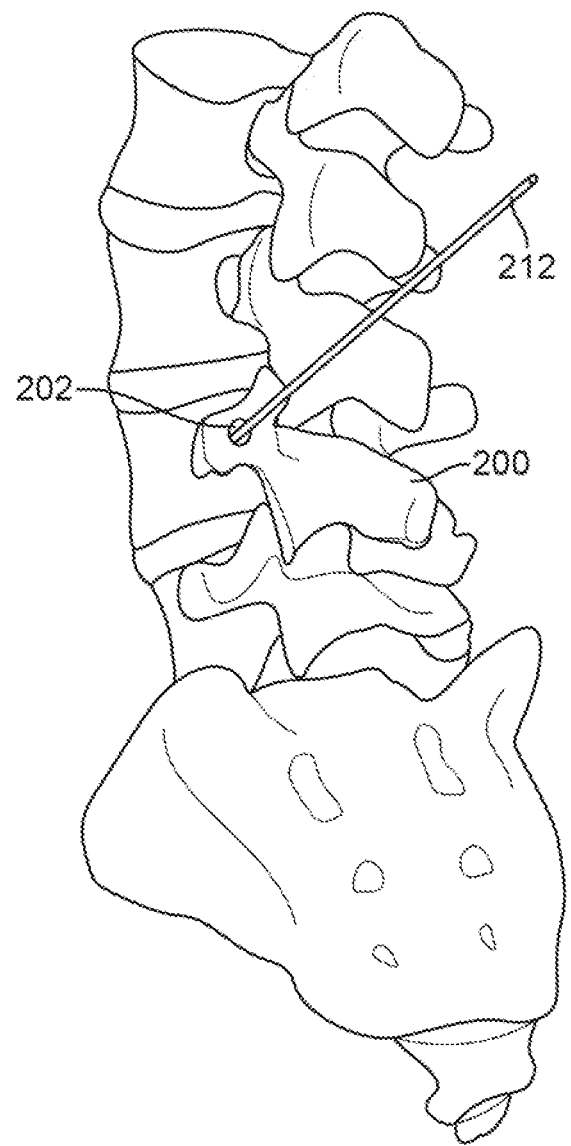

FIG. 8K shows the state of the procedure where the access device 100 is removed from the vertebral body 200 and pilot hole 202 leaving the bone cement (not shown) still within the cavity. The guidewire 212 can remain within the pilot hole 202 to allow for placement of a pedicle screw using preferred minimally invasive surgical techniques.

Figure 8L:
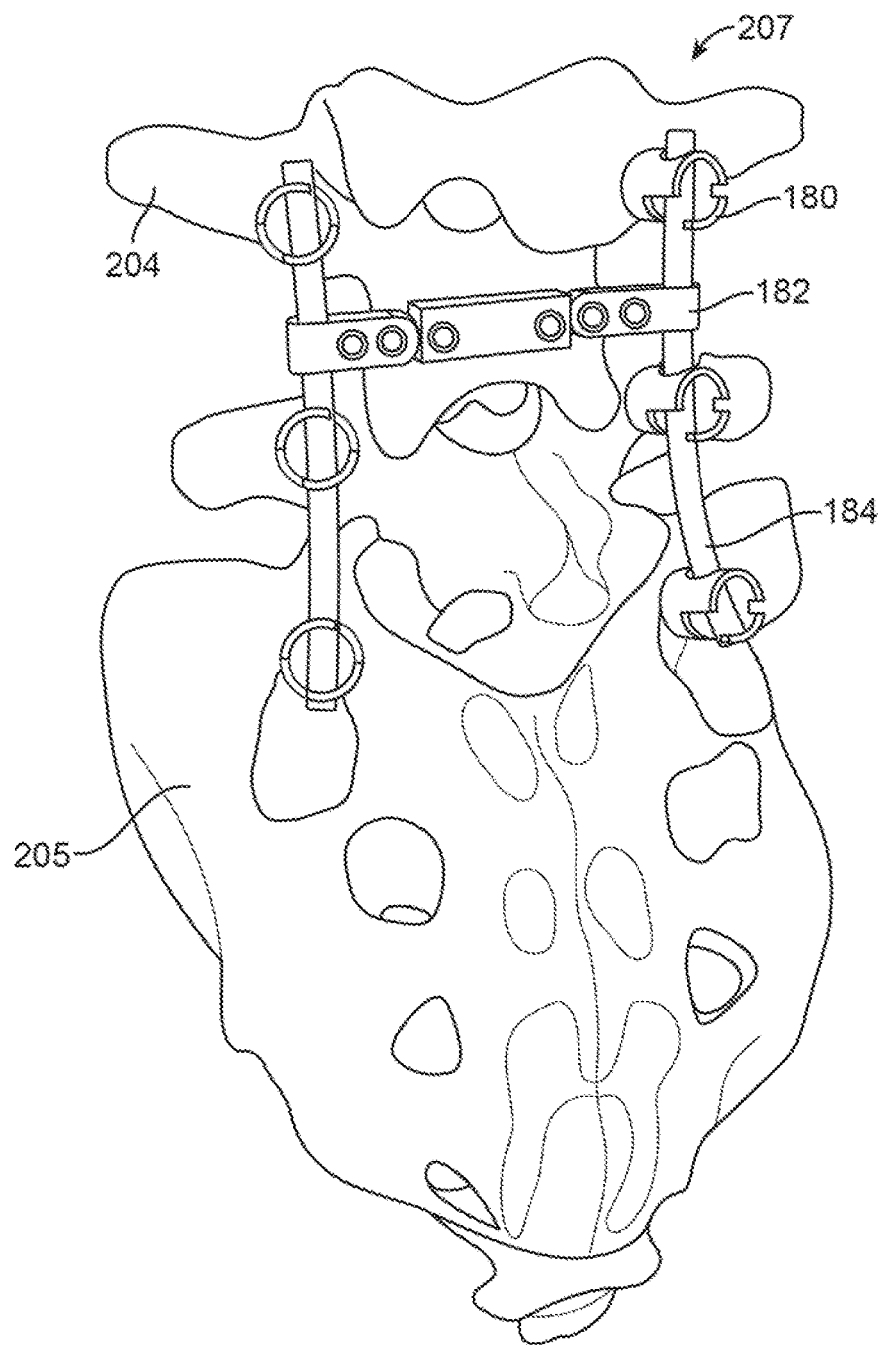
FIG. 8L shows an example of positioning implants within pilot holed filled with bone cement as discussed herein.

FIG. 8L illustrates a state of the lower portion of a vertebral column where the devices, methods and processes described herein provided cement to a number of sites within various structures in the vertebral column. As shown, implants, such as pedicle screws 180 placed within the hole (not shown in FIG. 8L) so that ultimately rods 184 and other implant supporting devices 182 can be positioned as needed. It is noted that the devices, methods, and processes described, herein can be used for treatment of a vertebral pedicle. However, the devices, methods, and processes can be used for any bone structure in the vertebral column such as the pedicle 204, vertebral body 207, sacrum 205 or even the coccyx 209.

The above and other features of the invention including various novel details of construction and combinations of parts, and other advantages, are described with reference to the accompanying drawings and the claims. It will be understood that the particular method and device embodying the invention are shown by way of illustration and not as a limitation of the invention. The principles and features of this invention may be employed in various and numerous embodiments without departing from the scope of the invention. Combination of aspects of the various embodiments or combinations of the various embodiments described herein are within the scope of this disclosure.

We claim:

1. A method of delivering a substance to an opening located in a bone of a vertebral column, the method comprising:
    advancing an access device to the bone, where the access device includes a delivery lumen extending along a longitudinal axis of the access device from a proximal opening to a distal port;
    actuating a shuttle mechanism of the access device to deploy an anchoring portion of the access device within the opening in the bone;
    anchoring the access device to the bone by engaging the anchoring portion against a wall portion of the bone surrounding the opening such that the delivery lumen creates a fluid path from the proximal opening through the distal port and into the opening;
    where the anchoring portion comprises an expandable structure such that anchoring the access device comprises forcing the expandable structure against a wall of the opening to secure the access device within the opening;
    where the expandable structure comprises a slotted portion of a slidable tube, and where the access device further comprises a radially protruding ramp portion, wherein anchoring the access device comprises advancing the slidable tube over the radially protruding ramp portion to cause the slotted portion to expand against the wall portion of the opening; and
    delivering the substance through the delivery lumen into the opening where the anchoring portion prevents rearward movement of the access device from the opening during delivery,
    wherein the ramp portion remains in contact with the slotted portion while the substance is delivered through the delivery lumen.

2. The method of claim 1, where advancing the access device to the bone comprises advancing the access device over a guidewire, where the guidewire is positioned within the opening in bone.

3. The method of claim 1, where the opening comprises an artificially created hole for securing an implant, the method further comprises positioning the implant within the hole.

4. The method of claim 1, where the delivery lumen extends through an inner tube and where the expandable structure comprises a slotted portion of a slidable tube located over the inner tube, and where the inner tube is affixed to the slidable tube at a distal location, wherein anchoring the access device comprises moving the inner tube relative to the slidable tube to cause the slotted portion to expand against the wall portion of the opening.

5. The method of claim 1, where the anchoring portion is formed on an end of a slidable tube, the shuttle mechanism operatively coupled to the slidable tube, where actuating the shuttle mechanism to deploy the anchoring portion further comprises actuating the shuttle mechanism to translate the slidable tube along the longitudinal axis of the access device.

6. The method of claim 5, where the anchoring portion comprises a radially expandable structure.

7. The method of claim 1, where the anchoring portion is formed on an end of an inner tube, the shuttle mechanism operatively coupled to a slidable tube surrounding the inner tube, where actuating the shuttle mechanism to deploy the anchoring portion further comprises actuating the shuttle mechanism to translate the inner tube along the longitudinal axis of the access device.

8. The method of claim 7, where the anchoring portion comprises a radially expandable structure.

9. The method of claim 1, where actuating the shuttle mechanism of the access device further includes rotating the shuttle mechanism about the longitudinal axis of the access device.

10. The method of claim 1, the method further comprising disengaging the anchoring portion from the wall portion of the bone after delivering the substance through the delivery lumen.

11. The method of claim 10, where disengaging the anchoring portion from the wall portion further includes actuating the shuttle mechanism to retract the anchoring portion into a tube of the access device.

12. The method of claim 10, where disengaging the anchoring portion from the wall portion further includes actuating the shuttle mechanism to advance a tube over the anchoring portion of the access device.

* * * * *